US00PP21836P2

(12) United States Plant Patent
Zaiger et al.

(10) Patent No.: US PP21,836 P2
(45) Date of Patent: Apr. 5, 2011

(54) NECTARINE TREE NAMED 'HONEY GEM'

(50) Latin Name: ***Prunus persica* var. *nucipersica***
Varietal Denomination: Honey Gem

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 12/657,173

(22) Filed: Jan. 15, 2010

(51) Int. Cl.
*A01H 5/00* (2006.01)

(52) U.S. Cl. ..... Plt./190

(58) Field of Classification Search ..... Plt./190
See application file for complete search history.

*Primary Examiner* — Annette H Para

(57) ABSTRACT

A new and distinct variety of nectarine tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular bearer of large size fruit.
2. Producing fruit that has a mild, sweet, sub-acid flavor with very good eating quality.
3. Producing fruit with good handling and shipping quality.
4. Fruit holding firm on the tree 8 to 10 days past maturity.
5. Vigorous and upright tree growth.

1 Drawing Sheet

Botanical classification: *Prunus persica* var. *nucipersica*.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarine trees, which are known to us, and mentioned herein are, 'Honey Royale' (U.S. Plant Pat. No. 12,008), 'Ruby Gold' (U.S. Plant Pat. No. 3,101) and two proprietary seedling selections '349LH508' and '6W60'.

STATEMENT REGARDING FEDERALLY SPONSORED RESEARCH AND DEVELOPMENT

Not applicable.

ORIGIN OF THE VARIETY

The new and distinct nectarine tree (*Prunus persica* var. *nucipersica*) was originated by us in our experimental orchard from seed of a first generation cross between a selected proprietary seedling with the field identification number '349LH508' and 'Honey Royale' Nectarine (U.S. Plant Pat. No. 12,008). The seed parent (349LH508) originated from a cross of a proprietary nectarine seedling (6W60) of unknown parentage and 'Ruby Gold' Nectarine (U.S. Plant Pat. No. 3,101). We planted and maintained under close and careful observation, a large group of these first generation seedlings on their own root system. One seedling, which is the present variety, exhibited desirable fruit characteristics and was selected in 2002 for additional asexual propagation and commercialization.

ASEXUAL REPRODUCTION OF THE NEW VARIETY

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of nectarine tree (*Prunus persica* var. *nucipersica*) is of large size, vigorous upright growth and a regular and productive bearer of large, firm, yellow flesh, clingstone fruit with good handling and shipping quality. The fruit is further characterized by having moderately juicy flesh with a mild, sweet, low acid flavor that has very good eating quality. In comparison to its seed parent (349LH508) the fruit of the new variety is larger in size and ripens approximately 12 days later. In comparison to its pollen parent 'Honey Royale' (U.S. Plant Pat. No. 12,008) the fruit of the new variety ripens approximately 24 days later.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 7 year old specimens grown near Modesto, Calif., with color in accordance with Munsell Book of Color.

Tree:

*Size.*—Large, pruned to 3 to 3.5 meters in height and width for economical harvesting of fruit. Varies with different cultural practices.

*Vigor.*—Vigorous, growth of 1 to 2 meters the first growing season, varies slightly with fertility of soil and climatic conditions.

*Form.*—Upright, usually pruned to vase shape.

*Branching habit.*—Upright, crotch angle approximately 35°. Crotch angle will increase with heavy crop load.

*Productivity.*—Productive, normal thinning and spacing necessary to develop desired market size fruit. Fruit set varies with climatic conditions during bloom time.

*Bearer.*—Regular, adequate fruit set six consecutive years. No alternate bearing observed.

*Fertility.*—Self-fertile.

*Density.*—Medium dense, pruning to open center of tree to vase shape desirable to enhance fruit color and keep fruit wood healthy.

*Hardiness.*—Hardy in all stone fruit growing areas of California. Tree grown in USDA Hardiness Zone 9. Winter chilling requirement approximately 600 hours at or below 45° F.

Trunk:

*Size.*—Large. Average circumference 43.2 cm at 22.9 cm above ground on a 7 year old tree.

*Stocky.*—Medium stocky.

*Texture.*—Medium shaggy, roughness increases with age.

*Color.*—Varies from 10YR 3/2 to 2.5Y 3/4.

Branches:

*Size.*—Medium. Average circumference 12.7 cm at 1.2 meters above ground.

*Surface texture.*—New growth relatively smooth. Mature growth medium rough, roughness increases with age.

*Lenticels.*—Average number 31 in a 25.8 sq cm area. Average length 3.4 mm. Average width 1.6 mm. Color varies from 7.5YR 5/8 to 10YR 5/8.

*Color.*—New growth varies from 2.5GY 6/6 to 10YR 4/4. Old growth varies from 7.5YR 2/4 to 10YR 2/2, varies with age of growth.

Leaves:

*Size.*—Large. Average length 142.4 mm. Average width 45.5 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins. Lower surface relatively smooth, with small ridges created by pinnate venation. Both surfaces glabrous.

*Petiole.*—Medium to large. Average length 13.4 mm. Average width 1.8 mm. Surface — glabrous. Longitudinally grooved. Color varies from 2.5GY 7/6 to 5GY 6/6.

*Glands.*—Reniform. Size — medium. Average length 1.5 mm. Average diameter 0.9 mm. Number varies from 2 to 5, average number 4. Located primarily on the base of leaf blade and upper portion of the petiole. Color varies from 2.5GY 7/6 to 2.5GY 6/6.

*Stipules.*—None observed on mature leaves.

*Color.*—Upper surface varies from 5GY 3/4 to 5GY 3/6. Lower surface varies from 5GY 5/4 to 5GY 4/4. Midvein color varies from 2.5GY 8/4 to 2.5GY 7/4.

Flower buds:

*Size.*—Large. Average length 16.3 mm. Average diameter 10.9 mm.

*Hardiness.*—Hardy in all stone fruit growing areas of California.

*Form.*—Plump, conical, becoming elongated before opening.

*Pedicel.*—Average length 3.5 mm. Average width 1.7 mm. Color varies from 10Y 7/6 to 2.5GY 7/6.

*Color.*—Varies from 5RP 7/8 to 7.5RP 6/12.

Flowers:

*Blooming period.*—Date of First Bloom Feb. 21, 2009. Date of Petal Fall Mar. 2, 2009, varies slightly with climatic conditions.

*Size.*—Large, showy. Average height 16.8 mm. Average diameter 35.0 mm.

*Petals.*—Number 5, alternately arranged to sepals. Orbicular, base narrows at point of attachment. Average length 18.5 mm. Average width 16.4 mm. Margin — sinuate, slightly cupped. Both upper and lower surfaces glabrous. Color varies from 5RP 8/4 to 5RP 7/6, fades with age of flower.

*Sepals.*—Number — 5, alternately arranged to petals. Average length 6.1 mm. Average width 5.0 mm. Shape — ovate, apex rounded. Margin — entire. Upper surface glabrous. Lower surface pubescent. Color of upper surface varies from 2.5GY 6/8 to 5R 3/6. Lower surface varies from 5R 3/2 to 5R 2/6.

*Stamens.*—Average number per flower 43. Average filament length 12.2 mm. Filament color varies from N 9.5/ (white) to 5RP 7/2 and 5RP 7/6, depending on age of flower. Anther color varies from 5R 3/10 to 7.5R 3/8.

*Pollen.*—Self-fertile. Color varies from 2.5Y 8/12 to 5Y 7/10.

*Pistil.*—Normally 1. Average length 17.3 mm. Surface glabrous. Position of stigma approximately 1.0 mm above anthers. Color varies from 7.5Y 7/6 to 10Y 8/6.

*Fragrance.*—Wanting.

*Color.*—Varies from 5RP 8/4 to 5RP 7/8.

*Number flowers per flower bud.*—Normally one.

*Pedicel.*—Average length 4.1 mm. Average width 1.7 mm. Color varies from 2.5GY 6/6 to 5GY 7/6.

Fruit:

*Maturity when described.*—Firm ripe.

*Date of first picking.*—Aug. 3, 2009.

*Date of last picking.*—Aug. 10, 2009, varies slightly with climatic conditions.

*Size.*—Large. Average diameter axially 76.0 mm. Average transversely in suture plane 78.1 mm. Average weight 272.6 grams, varies slightly with fertility of the soil, amount of thinning and climatic conditions.

*Form.*—Globose.
*Suture.*—Shallow, extends from base to apex.
*Ventral surface.*—Nearly smooth to very slightly lipped.
*Apex.*—Rounded to slightly retuse.
*Base.*—Rounded to slightly retuse.
*Stem cavity.*—Rounded to slightly elongated in suture plane. Average depth 11.0 mm. Average diameter 16.2 mm.

Stem:
*Size.*—Medium. Average length 9.0 mm. Average diameter 3.0 mm.
*Color.*—Varies from 7.5Y 6/8 to 10Y 7/6.

Flesh:
*Ripens.*—Evenly.
*Texture.*—Firm, meaty.
*Fibers.*—Few, small, tender.
*Firmness.*—Firm, holds firm on the tree 8 to 10 days after maturity (shipping ripe).
*Aroma.*—Slight to moderate.
*Amydgalin.*—Undetected.
*Eating quality.*—Very good.
*Flavor.*—Very good, mild sweet, sub-acid.
*Juice.*—Moderate amount, enhances flavor.
*Brix.*—Average 17.7°, varies slightly with amount of fruit per tree and climatic conditions.
*Color.*—Varies from 2.5Y 8/10 to 5Y 8/8. Pit cavity varies from 2.5Y 8/8 to 7.5R 3/10, with slight bleeding into the flesh.
*Pit cavity.*—Average length 43.4 mm. Average width 28.1 mm.

Skin:
*Thickness.*—Medium.
*Surface.*—Smooth.
*Pubescence.*—Wanting.
*Tendency to crack.*—None.
*Color.*—Ground color varies from 2.5Y 8/10 to 5Y 8/10. Overspread with 7.5R 3/10 to 7.5R 2/8 on approximately 80% of fruit surface.
*Tenacity.*—Tenacious to flesh.
*Astringency.*—None.

Stone:
*Type.*—Clingstone.
*Size.*—Large. Average length 42.9 mm. Average width 25.3 mm. Average thickness. 23.8 mm.
*Form.*—Ovoid.
*Base.*—Usually flat, varies from flat to slightly rounded.
*Apex.*—Slightly pointed. Average length 3.0 mm.
*Surface.*—Pitted throughout, pits vary from rounded to slightly elongated. Ridges extend from base to apex.
*Sides.*—Unequal, one side is slightly larger, extending further from suture plane.
*Ridges.*—Relatively smooth with wide surface.
*Tendency to split.*—None.
*Color.*—Varies from 7.5YR 3/4 to 10R 2/6.

Kernel:
*Size.*—Large. Average length 21.2 mm. Average width 13.1 mm. Average depth 6.1 mm.
*Form.*—Ovate.
*Viability.*—Good, complete embryo development.
*Skin.*—Color varies from 5Y 9/6 to 5Y 8/8.

Use: Dessert.
*Market.*—Local and long distance.

Keeping quality: Good, held firm in cold storage at 38° to 42° F. for 2 weeks without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, substantially as illustrated and described.

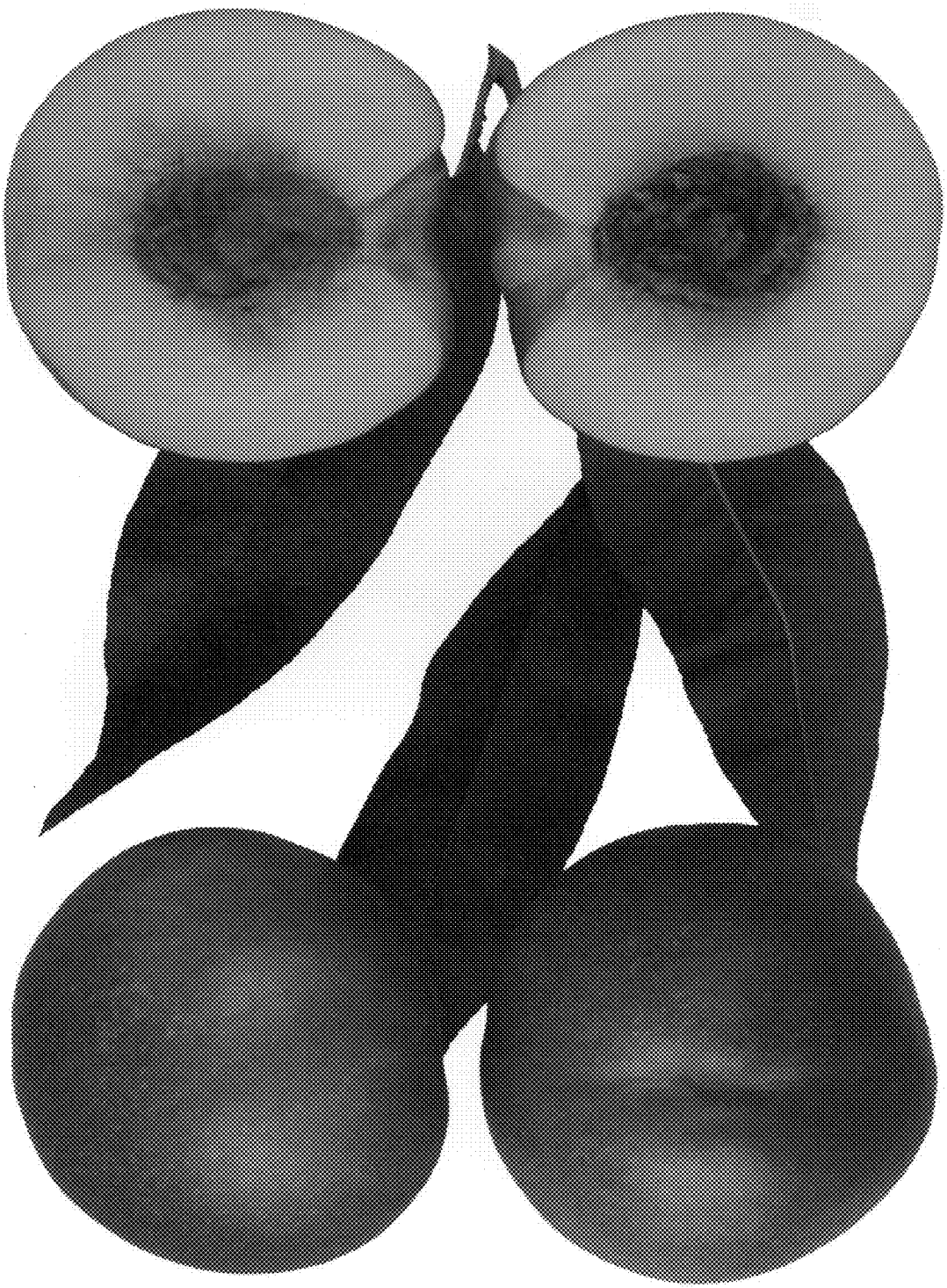

* * * * *